United States Patent [19]

Naganuma et al.

[11] Patent Number: 4,594,242

[45] Date of Patent: Jun. 10, 1986

[54] DENTIFRICE COMPOSITION

[75] Inventors: Takeshi Naganuma; Natsumi Miyagawa, both of Odawara; Toshiyuki Ozawa, Chigasaki; Kazutoshi Tamura, Hiratsuka, all of Japan

[73] Assignee: Lion Corporation, Tokyo, Japan

[21] Appl. No.: 689,892

[22] Filed: Jan. 9, 1985

[30] Foreign Application Priority Data

Mar. 8, 1984 [JP] Japan .................................. 59-44651

[51] Int. Cl.⁴ .......................... A61K 7/16; A61K 7/20
[52] U.S. Cl. ...................................... 424/57; 433/216; 514/835; 424/49
[58] Field of Search .......................... 424/57; 433/216; 514/835

[56] References Cited

U.S. PATENT DOCUMENTS

| | | | |
|---|---|---|---|
| 3,012,852 | 12/1961 | Nelson | 424/57 |
| 3,066,056 | 11/1962 | Schlaeger et al. | 424/57 |
| 3,169,096 | 2/1965 | Schlaeger et al. | 424/57 |
| 4,024,239 | 5/1977 | Pader | 424/57 |
| 4,170,634 | 10/1979 | Cordon et al. | 424/57 |
| 4,322,207 | 3/1982 | Madsen | 433/216 |
| 4,343,786 | 8/1982 | Baines et al. | 424/52 |
| 4,394,371 | 7/1983 | Barberio | 424/57 |

FOREIGN PATENT DOCUMENTS 53-124631 10/1978 Japan .................................... 424/57

Primary Examiner—Ronald W. Griffin
Attorney, Agent, or Firm—Birch, Stewart, Kolasch & Birch

[57] ABSTRACT

A dentifrice composition comprising calcium hydrogenphosphate anhydride whose crystallite has an average size of 300 to 3,500 angstroms as measured by X-ray diffractometry and an aluminum oxide having an average particle size of 0.5 to 10 μm is disclosed. The composition have an excellent cleaning ability and mild abrading property not causing damage of tooth enamel and gives good luster to teeth.

11 Claims, No Drawings

DENTIFRICE COMPOSITION

BACKGROUND OF THE INVENTION

This invention relates to a dentifrice composition having an excellent cleaning ability and mild abrading property not causing damage of tooth enamel and giving good luster to teeth.

In general, abrasives for use in dentifrice compositions are required to have an increased ability of efficiently removing stain, dental plaque, and food debris adhered to or deposited on teeth with the aid of physical action, that is, an improved cleanability as a tooth cleaning agent, and to exhibit mild abrasiveness to such an extent that the tooth enamel will not be damaged, as well as to prevent deposition of dental plaque and calculus. Abrasives are also required to give luster to the tooth surface.

In this case, the efficiency of physical removal of stain, plaque, and food debris can be increased by using an abrasive having increased abrasiveness. Particularly, it has been a common practice in the prior art to enhance the cleaning effect of an abrasive on the tooth surface by increasing the abrasiveness thereof. However, increasing abrasiveness is generally opposite to the prevention of damage to the tooth surface. The higher the abrasiveness, the greater is the likelihood that the tooth surface would be abraded away. Particularly when brushing is done inadequately, there is the increased likelihood that wedge-shaped deffects would be formed and the tooth surface would be marred or scratched and reduced in luster.

Conventionally, an abrasive has been combined with a luster agent in order to give luster to a tooth surface and to smooth it, thereby preventing plaque and deposition of dental calculus. However, luster agents which conventionally are said to have luster-improving effect, although causing effect by themselves or in combination with an abrasive having almost no abrading property, cause no luster-improving effect in combination with an abrasive having high abrading property such as calcium hydrogenphosphate anhydride.

SUMMARY OF THE INVENTION

The object of this invention is to provide a dentifrice composition which does not cause damage to a tooth surface, has a proper abrading property causing excellent cleaning effect and can give luster to a tooth surface.

As a result of extensive investigations to meet the above-mentioned need, the inventors have found that calcium hydrogenphosphate anhydride (secondary calcium phosphate anhydride) whose crystallite has an average size of 300 to 3,500 angstroms as measured by X-ray diffractometry, and preferably, which has a density of 2.650 to 2.885 g/cm$^3$, a specific surface area of 2.5 to 20 m$^2$/g as measured by the BET (Brunauer-Emmett-Teller) method, and an average particle size of 2 to 30 $\mu$m has good physical properties as an abrasive, and that when the above-defined calcium hydrogenphosphate anhydride is used as an abrasive in combination with aluminum oxide having an average particle size of 0.5 to 10 $\mu$m in an oral composition, the resulting oral composition is improved in cleaning action without increasing its abrasiveness and gives excellent luster to teeth.

It was difficult in the prior art to enhance the cleaning action and to lower the abrading action of an abrasive at the same time inasmuch as the cleaning action of conventional abrasives in substantially proportional to the abrading action thereof, and it is thus imperative for cleaning enhancement to increase abrading action. On the contrary to such conventional belief, the inventors have found that calcium hydrogenphosphate anhydride having crystallites of a size having an average value of 300 to 3,500 angstroms as measured by X-ray diffractometry exhibits improved cleaning action irrespective of its low abrasiveness as demonstrated in experiments to be described later, and thus, the use of this calcium hydrogenphosphate anhydride in combination with aluminum oxide having an average particle size of 0.5 to 10 $\mu$m is sufficiently effective to clean up the tooth without impairing the dental enamel, meeting both the requirements of high cleanability and low abrasiveness at the same time as well as to achieve high tooth-luster-improving effect.

It is well known in the art to use calcium hydrogenphosphate anhydride (secondary calcium phosphate anhydride) as an abrasive for dentifrices. However, such previously used calcium hydrogenphosphate anhydride usually has an average crystallite size of 3,800 to 4,300 angstroms as measured by X-ray diffractometry, a specific surface area of about 1 to 2 m$^2$/g as measured by the BET method, and a density of 2.890 g/cm$^3$, and as a result, exhibits too high abrasiveness as shown in experiments to be described later. When such conventional calcium hydrogenphosphate anhydride is used alone as an abrasive, the resulting oral composition will show an abrasiveness value of above 250, as measured by the RDA (Radioactive Dentin Abrasion) method, which value is generally regarded as the upper limit by the ADA (American Dental Association) and other dental associations, and thus has the possibility of inducing wedgeshaped defects after long term repeated use if the brushing way is inadequate. As compared with the conventional ones, the calcium hydrogenphosphate anhydride (secondary calcium phosphate anhydride) of the present invention has an average crystallite size of 300 to 3,500 angstroms as measured by X-ray diffractometry, has less sharp edges or more round edges, exhibits extremely low abrading action so that it can be used as a sole abrasive, and exhibits more cleaning action (or stain removing action) than other types of abrasive having a similar degree of abrasiveness, with the additional benefit of making the tooth aesthetically white. When the above-mentioned specific calcium hydrogenphosphate anhydride is combined with the above-mentioned specific aluminum oxide, high tooth-luster-improving effect is exerted.

According to this invention, a dentifrice composition is provided which is characterized by containing both calcium hydrogenphosphate anhydride whose crystallite has an average size of 300 to 3,500 angstroms as measured by X-ray diffractometry and aluminum oxide having an average particle size of 0.5 to 10 $\mu$m.

According to a preferred embodiment of this invention, a dentifrice composition is provided in which aluminum oxide with an alpha phase content of below 93% is combined with the above calcium hydrogenphosphate anhydride. Use of aluminum oxide with an alpha phase content of below 93% enables the provision of a dentifrice composition which can give higher luster to a tooth surface.

Describing this point in more detail, "dentifrices containing ground crystals of alpha-alumina having a mean ultimate particle size of about 1 to 2 microns" is disclosed in U.S. Pat. No. 4,060,599. However, use of α-alumina, or aluminum oxide with an alpha phase content of 100%, can not achieve sufficient tooth-surface-luster-improving effect. In contrast, use of aluminum oxide with an alpha phase content of below 93% can achieve excellent tooth-surface-luster-improving effect.

The following description will clarify the above and the other objects as well as the characteristics and the advantages of this invention.

DETAILED DESCRIPTION OF THE INVENTION

The dentifrice composition according to this invention is obtained by the combination of aluminum oxide and calcium hydrogenphosphate anhydride (secondary calcium hydrogenphosphate anhydride) whose crystallite has an average size (also referred to as "average crystallite size" herein) of 300 to 3,500 angstroms as measured by X-ray diffractometry as will be demonstrated in the experiment shown below, and has a proper abrading action and a high cleaning action on teeth and gives a good luster-improving effect to teeth as previously mentioned.

The calcium hydrogenphosphate anhydride which is useful in the present invention has an average crystallite size of 300 to 3,500 angstroms, with one having an average crystallite size of 300 to 3,000 angstroms being particularly preferred for improved cleaning action. If the average crystallite size is less than 300 angstroms, the phosphate shows too low cleaning action, and if the average crystallite size is more than 3,500 angstroms, the phosphate shows too high abrasiveness, both failing to achieve the objects of the invention.

Preferably, the calcium hydrogenphosphate anhydride useful in the present invention has a density of 2.650 to 2.885 g/cm$^3$, more preferably 2.750 to 2.885 g/cm$^3$ at 20° C., a specific surface area of 2.5 to 20 m$^2$/g, more preferably 3 to 10 m$^2$/g as measured by the BET method, and an average particle size of 2 to 30 μm, more preferably 5 to 25 μm as measured by laser light-scattering photometry.

The term "density" used herein is a measurement using a pycnometer followed by calculation according to the following formula:

$$\rho_P = \frac{M_S - M_O}{(M_L - M_O) - (M_{SL} - M_S)} \cdot \rho_L$$

where
- $M_S$: the weight of the pycnometer plus the weight of a powder sample,
- $M_O$: the weight of the pycnometer,
- $M_L$: the weight of the pycnometer filled with liquid (water),
- $M_{SL}$: the weight of the pycnometer filled with a powder sample and further with liquid (water), that is, [pycnometer weight + powder weight + liquid weight],
- $\rho_L$: the density of the liquid (water) at 20° C., and
- $\rho_p$: the density of the powder at 20° C.

The calcium hydrogenphosphate anhydride useful herein is preferably in the form of a cohesive aggregate of plate crystals having an average primary particle size of 0.1 to 5 μm because of its excellently improved juice effect. In this case, the average value of the size of primary particles is obtained from a measurement on an electron micrograph followed by calculation. More preferably, the above-defined calcium hydrogenphosphate anhydride has a structure in which plate of flake crystals aggregate or closely stack one on top of another like a pine cone to form a cohesive body with or without microfine particles or indefinite crystalline structure.

The calcium hydrogenphosphate anhydride useful in the present invention is also preferably in the form of a spherulitic calcium hydrogenphosphate anydride having an average roundness of 0.45 to 0.95, more preferably 0.5 to 0.9 (Wadell, J., Geol., 40 (1932), 443–451) because it gives little gritty feel and thus gives a pleasant feel to the mouth as well as an improved lustering effect.

The calcium hydrogenphosphate anhydride of the present invention may be prepared in a conventional way, for example, by adding in the neutralizing reaction between phosphoric acid and lime milk a crystallization modifier capable of controlling the growth of crystals or effecting on crystal growth-kinetics, crystal habit and specific growth rates of individual crystal faces, as disclosed in U.S. Pat. Nos. 2,287,699 (1942), 3,012,852 (1961), 3,066,056 (1962), and 3,169,096 (1965), and Japanese Patent Publication No. 39-3272 and 39-3273 (1964). In this case, the crystallization modifiers used may preferably be phosphoric acid condensates and salts thereof, and be added in the course of neutralizing reaction between phosphoric acid and lime milk. Also preferably, the amount of the crystallization modifier added ranges from 0.1 to 40% by weight, more preferably from 0.5 to 30% by weight based on the weight of the calcium hydrogenphosphate anhydride produced. As the amount of the modifier added increases, the growth of crystals is retarded and the size of crystallites becomes smaller. If the amount of the modifier added is less than 0.1% by weight, then crystallites will grow larger beyond the average size of 3,500 angstroms and result in increased abrasiveness. If the amount of the modifier added is more than 40% by weight, then crystallites will become smaller below the average size of 300 angstroms and will not exhibit low abrasion and high cleaning performance. The calcium hydrogenphosphate anhydride of the present invention may be prepared in a variety of grades by properly controlling the amount of the crystallization modifier added, the point and rate of addition of the modifier, phosphoric acid concentration, reaction temperature, reaction time, agitation speed and other parameters in the preparation procedure.

In the composition according to this invention, aluminum oxide is blended in addition to the above-mentioned specific calcium hydrogenphosphate anhydride in order to achieve excellent lustering effect through the combination of these compounds.

It is necessary that the average particle size of aluminum oxide is 0.5 to 10 μm, preferably 0.5 to 5 μm in order for the composition to exhibit good tooth-luster-improving effect. On the contrary, an average particle size of less than 0.5 μm results in small abrading action, causing almost no changes in the enamel surface and not increasing the degree of luster, while an average particle size of larger than 10 μm causes damage (scratches) to enamel surface, lowering its luster. In this case, it is preferred that aluminum oxide having the average particle size within the above specified range does not contain large particles of more than 10 μm, preferably more than 5 μm. Aluminum oxide having the average particle size within the required range but containing large particles of more than 10 μm, may reduce the luster-improving effect of the composition.

In the present invention, it is preferred that the alpha phase content of aluminum oxide is not higher than 93%, preferably between 90% and 10% and more preferably between 85% and 15%. Use of this kind of aluminum oxide can give excellent luster to tooth surface and can achieve a proper abrading action and a good cleaning action.

The aluminum oxide with an alpha phase content of below 93% refers to one which consists of proper proportions of $\alpha$-$Al_2O_3$, $\gamma$-$Al_2O_3$, amorphous $Al_2O_3$ and the like and indicates a peak below 93% of that of aluminum oxide with an alpha phase content of 100% ($\alpha$-$Al_2O_3$) in X-ray diffraction. More detailedly, when the average of the ratios of the intensities of X-rays diffracted by the (012) surface and the (116) surface of aluminum oxide to those of X-rays diffracted by the same surfaces of $\alpha$-$Al_2O_3$ is below 93%, the aluminum oxide is called as aluminum oxide with an alpha phase content of below 93%.

Aluminum oxide with the above alpha phase content can be manufactured according to the Bayer's process. Anhydrous alumina with a desired alpha phase content can be obtained by appropriately controlling the sintering temperature in the manufacturing process of the Bayer's method.

It is preferred that the amount of the above calcium hydrogenphosphate anhydride blended is 1 to 60% by weight, preferably 5 to 50% by weight of the total amount of the composition. It is preferred that the amount of aluminum oxide blended is 0.1 to 30% by weight, preferably 0.3 to 10% by weight of the total amount of the composition. Moreover, in attaining the purpose of this invention, it is preferred that the ratio by weight of calcium hydrogenphosphate anhydride to aluminum oxide is 100:0.2 to 100:60, preferably 100:0.6 to 100:20.

The dentifrice composition of this invention may contain any desired other ingredients depending on the type of the composition.

For example, binders such as sodium carboxymethyl cellulose, hydroxyethyl cellulose, alginates, carrageenan, gum arabic, polyvinyl alcohol, etc.; humectants such as polyethylene glycol, sorbitol, glycerin, propylene glycol, etc.; surface active agents such as sodium lauryl sulfate, sodium dodecylbenzenesulfonate, sodium hydrogenated coconut fatty acid monoglyceride monosulfate, sodium lauryl sulfoacetate, sodium N-lauroylsarcosinate, N-acylglutamates, lauroyl diethanolamide, sucrose fatty acid esters, etc.; flavoring agents, for example, essential oils such as peppermint oil, spearmint oil, etc. and flavors such as l-menthol, carvone, eugenol, anethol, etc.; sweeteners such as sodium saccharin, stevioside, neohesperidyl dihydrochalcone, glycyrrhizin, perillartine, p-methoxycinnamic aldehyde, somatine, etc.; preservatives; and pharmaceutical agents such as lysozyme chloride, dextranase, bacteriolytic enzymes, mutanase, chlorhexidine and salts thereof, sorbic acid, alexidine, hinokitiol, cetyl pyridinium chloride, alkyl glycines, alkyl diaminoethyl glycine salts, allantoin, ε-aminocaproic acid, tranexamic acid, azulene, vitamin E, sodium monofluorophosphate, sodium fluoride, stannous fluoride, water-soluble primary and secondary phosphoric acid salts, quaternary ammonium compounds, sodium chloride, etc.

In the present invention, in addition to the calcium hydrogenphosphate anhydride (secondary calcium phosphate anhydride) abrasive of the present invention and the aluminum oxide, any other conventional abrasives may be blended including calcium hydrogenphosphate dihydrate, conventional calcium hydrogenphosphate anhydride having an average crystallite size of 3,800 to 4,300 angstroms (falling outside the scope of the invention), calcium carbonate, calcium pyrophosphate, insoluble sodium metaphosphate, amorphous silica, crystalline sillica, precipitated silica, aluminosilicate, aluminun hydroxide, microcrystalline cellulose, resin, tertiary magnesium phosphate, magnesium carbonate, tertiary calcium phosphate, titanium dioxide, etc. and mixtures thereof, as long as the effects of the present invention are not harmed.

In a dentifrice composition of this invention, the content of the abrasive may be in the range of 5 to 95% by weight, preferably 10 to 90% by weight of the composition. The content of the binder may be in the range of 0.1 to 5% by weight, preferably 0.3 to 3% by weight of the composition. The content of the humectant may be in the range of 1 to 70% by weight, preferably 10 to 60% by weight of the composition. The content of the surface active agent may be in the range of 0.1 to 10% by weight, preferably 0.2 to 5% by weight of the composition. The content of the flavor may be in the range of 0.1 to 5% by weight, preferably 0.3 to 2% by weight of the composition. The content of the sweetner may be in the range of 0.001 to 5% by weight, preferably 0.005 to 2% by weight of the composition.

A dentifrice composition of the invention is prepared by blending the calcium hydrogenphosphate anhydride and aluminum oxide into a dentifrice composition or mixing it with the other ingredients according to the conventional method.

In order that those skilled in the art will more readily understand the invention, some exemplary procedures for preparing the calcium hydrogenphosphate anhydride of the invention will be presented below.

PREPARATION 1

Lime water is prepared by heating 3 liters of an aqueous solution having 4.0 grams of magnesium chloride dissolved therein to 80° C., pouring 380 grams of quick lime into the solution with stirring, and continuing stirring for 30 minutes to allow the quick lime to be slaked. The reaction mixture is passed through 100 mesh screen to remove coarse particles, obtaining lime water having a converted concentration of 124 grams of calcium oxide per liter.

Then, one liter of an aqueous solution of 75% phosphoric acid is heated to 75° C., and the above-prepared lime water is added to the solution at a rate of 600 milliliters/hour with stirring. At the point when the pH value of the reaction mixture has reached 2.2, pyrophosphoric acid having a $P_2O_5$ content of 80% is additionally added at a rate of 0.3 grams/minute concurrently with the addition of lime water. When the pH value has reached 2.8, the addition of pyrophosphoric acid is terminated. The addition of lime water is further continued until the pH value of the reaction solution reaches 5.0. The reaction solution is then filtered, and the filter cake is washed with water and dried at 60° C. for 24 hours. It was found that by varying the amount of a polyphosphoric acid or its salt, such as pyrophosphoric acid or sodium pyrophosphate added and controlling the starting point and rate of addition of a polyphosphoric acid or its salt, there can be obtained calcium hydrogenphosphate anhydride having correspondingly varying crystallite size, density and specific surface area.

PREPARATION 2

Lime water is prepared by heating 3 liters of an aqueous solution having 3.7 grams of magnesium chloride dissolved therein to 80° C., pouring 390 grams of quick lime into the solution with stirring, and continuing stirring for 30 minutes to allow the quick lime to be slaked. The reaction mixture is passed through the 100 mesh screen to remove coarse particles, obtaining lime water having a converted concentration of 128 grams of calcium oxide per liter.

Then, one liter of an aqueous solution of 75% phosphoric acid is heated to 78° C., and the above-prepared lime water is added to the solution at a rate of 570 milliliters/hour with stirring. At the point when the pH value of the reaction mixture has reached 0.8, pyrophosphoric acid is additionally added concurrently with the addition of lime water. When the pH value has reached 1.2, the addition of pyrophosphoric acid is terminated. The addition of lime water is further continued until the pH value of the reaction solution reaches 5. The total amount of lime water added is 5.3 liters, and the amount of pyrophosphoric acid added is 13.5 grams. This means that pyrophosphoric acid is added in an amount of 2.0 parts by weight per 100 parts by weight of calcium oxide. The reaction solution is then filtered, and the filter cake is washed with water and dried at 60° C. for 24 hours, obtaining calcium hydrogenphosphate anhydride within the scope of the present invention.

Experimental Examples are presented below in order to illustrate the effects of the calcium hydrogenphosphate anhydride of the present invention.

EXPERIMENTAL EXAMPLE 1

A number of calcium hydrogenphosphate samples having different average crystallite sizes and average particle size shown in Tables 1 and 2 were tested for abrasiveness and cleanability by the following methods, in order to examine the correlation between size and performance of abrasives. The calcium hydrogenphosphate anhydride samples used had a specific surface area of 2.5 to 20 m$^2$/g as measured by the BET method, and a density of 2.650 to 2.885 g/cm$^3$. The results are shown in Table 3.

The average crystallite size is measured by carrying out X-ray diffraction analysis on a powder sample. Based on the broadening of peaks, the crystallinity of the powder sample is quantitatively expressed using the size of crystallites as an index. Cu-K$\alpha$ ray is used for measurement as the X-ray source, and the data of X-ray diffraction are analyzed for non-overlapping predominant peaks using Scherrer's equation $D = K\lambda/\beta \cos \theta$, determining the average size of crystallites. In this case, the predominant peaks selected are $2\theta = 53.1°$, 49.3°, 47.3°, 36.1°, 32.9°, 32.6°, 31.1°, 30.25°, 28.65°, and 13.15°, and they are averaged. In the above equations, $D$ is the size of a crystallite (in angstrom), $\lambda$ is the wavelength of X-ray used for measurement (in angstrom), $\beta$ is the spread of diffracted rays purely based on the size of crystallites (in radian) (the reference used is an $\alpha$-Al$_2$O$_3$ powder fired at 1,100° C. for 24 hours), K is shape factor (constant, 0.9 in this measurement), and $\theta$ is the Bragg angle of diffracted rays. It is to be noted that $\beta$ is an experimentally determined half-value-width minus the half-value-width of a highly crystallite material measured under the same conditions.

ABRASIVENESS MEASUREMENT

The RDA (Radioactive Dentin Abrasion) value was measured according to the process described in Hefferen, *J. Dent. Res.*, Vol. 55, No. 4, pp. 563–573.

CLEANABILITY MEASUREMENT

Tobacco tar was collected in a conventional manner and dissolved in a suitable solvent. The tar solution was uniformly coated onto a tile and dried by heating. The tar-coated tile was placed in a polishing tank and brushed 2,000 times under a load of 200 grams using a suspension of 5 grams of a powder (each calcium hydrogenphosphate sample shown in Tables 1 and 2) in 15 grams of an aqueous solution of 60% glycerin containing 0.3% of sodium carboxymethyl cellulose. At the end of polishing, the tile was visually observed to determine the percent removal of tar therefrom.

The brush used is a commercially available tooth brush having 44 bundles of bristles, a bristle diameter of 8 mils (about 0.2 mm), and a bristle length of 12 mm, made of nylon-62, with the brush hardness designated M (medium) according to the Japanese household product quality indication.

| Evaluation criterion for tar removal | |
|---|---|
| Point | Percentage removal of tobacco tar |
| 1 | 0–10% |
| 2 | 11–20% |
| 3 | 21–30% |
| 4 | 31–40% |
| 5 | 41–50% |
| 6 | 51–60% |
| 7 | 61–70% |
| 8 | 71–80% |
| 9 | 81–90% |
| 10 | 91–100% |

TABLE 1

| | DCP-D (calcium hydrogenphosphate dihydrate) | | |
|---|---|---|---|
| Sample | Average crystallite size (Å) | Average particle size* (μm) | |
| No. 1 | — | 9 | Comparison |
| No. 2 | — | 14 | Comparison |

TABLE 2

| | DCP-A (calcium hydrogenphosphate anhydride) | | |
|---|---|---|---|
| Sample | Average crystallite size (Å) | Average particle size* (μm) | |
| No. 3 | 4150 | 2** | Comparison |
| No. 4 | 4150 | 16 | " |
| No. 5 | 282 | 13 | " |
| No. 6 | 3810 | 18 | " |
| No. 7 | 375 | 22 | Invention |
| No. 8 | 661 | 10 | " |
| No. 9 | 867 | 7 | " |
| No. 10 | 1660 | 13 | " |
| No. 11 | 2070 | 15 | " |
| No. 12 | 3194 | 10 | " |

*The average particle size was measured using a particle size distribution measuring instrument, Microtrac (trade name, available from Leed & Northrup Company).
**obtained by sieving conventional DCP-A and collecting a fraction having an average particle size of 2 microns.

TABLE 3

Abrasiveness and cleanability of various calcium hydrogenphosphate samples

| Sample | Mixing ratio | Abrasiveness (RDA value) | Cleanability | |
|---|---|---|---|---|
| DCP-D No. 1 | — | 50 | 2.4 | Comparison |
| DCP-D No. 2 | — | 57 | 2.6 | " |
| DCP-A No. 3 | — | 135 | 4.3 | " |
| DCP-A No. 4 | — | ≧250 | 7.3 | " |
| DCP-D No. 2/ DCP-A No. 4 | 8/2 | 140 | 4.5 | " |
| DCP-D No. 2/ DCP-A No. 4 | 5/5 | 218 | 6.0 | " |
| DCP-A No. 5 | — | 125 | 3.2 | " |
| DCP-A No. 6 | — | ≧250 | 6.8 | " |
| DCP-A No. 7 | — | 118 | 4.9 | Invention |
| DCP-A No. 8 | — | 145 | 6.1 | " |
| DCP-A No. 9 | — | 134 | 5.3 | " |
| DCP-A No. 10 | — | 155 | 6.3 | " |
| DCP-A No. 11 | — | 151 | 6.8 | " |
| DCP-A No. 12 | — | 180 | 7.5 | " |
| DCP-D No. 2/ DCP-A No. 10 | 5/5 | 153 | 6.1 | " |
| DCP-D No. 2/ DCP-A No. 11 | 9/1 | 86 | 4.0 | " |
| DCP-D No. 2/ DCP-A No. 11 | 5/5 | 141 | 6.5 | " |
| DCP-D No. 2/ DCP-A No. 8 | 5/5 | 101 | 5.0 | " |

EXPERIMENTAL EXAMPLE 2

Calcium hydrogenphosphate samples having different densities and specific surface areas shown in Table 4 were examined for abrasiveness and cleanability by the following procedure in order to establish the correlation between performance and physical properties. The results are also shown in Table 4. The density was obtained by a measurement using a pycnometer followed by calculation as previously described.

ABRASIVENESS MEASUREMENT

Using a suspension of 5 grams of a powder (each calcium hydrogenphosphate sample shown in Table 4) in 15 grams of an aqueous solution of 60% glycerin containing 0.3% of sodium carboxymethyl cellulose, a copper plate having a Vickers hardness of 120 as prescribed in Japanese Industrial Standard H-3361 was brushed 20,000 times for 2 hours under a load of 200 grams in a horizontal abrasion tester. The brush used was the same as used in Experimental Example 1. The abrasivity on the copper plate was measured in milligram.

CLEANABILITY MEASUREMENT

Cleanability was determined in the same manner as in Experimental Example 1.

TABLE 4

| Sample* | Average particle size (μm) | Mixing ratio by weight | Average crystallite size (Å) | Density (g/cm³) | Specific surface area** (m²/g) | Abrasivity on copper plate (mg) | Cleanability | |
|---|---|---|---|---|---|---|---|---|
| DCP-D No. 1 | 9 | — | — | 2.320 | — | 0.8 | 2.3 | Comparison |
| DCP-D No. 2 | 14 | — | — | 2.320 | — | 1.2 | 2.5 | " |
| DCP-A No. 3 | 2*** | — | 4150 | 2.890 | 4.4 | 17.3 | 4.3 | " |
| DCP-A No. 4 | 16 | — | 4150 | 2.890 | 1.2 | 47.0 | 7.3 | " |
| DCP-D No. 2/DCP-A No. 4 | | 8/2 | — | — | — | 18.5 | 4.5 | " |
| DCP-D No. 2/DCP-A No. 4 | | 5/5 | — | — | — | 31.4 | 6.0 | " |
| DCP-A No. 16 | 25 | — | 230 | 2.615 | 28.6 | 1.3 | 2.9 | " |
| DCP-A No. 17 | 15 | — | 830 | 2.706 | 13.2 | 1.5 | 5.6 | Invention |
| DCP-A No. 18 | 10 | — | 1600 | 2.810 | 8.9 | 4.7 | 5.9 | " |
| DCP-A No. 19 | 13 | — | 2850 | 2.861 | 3.0 | 11.3 | 6.6 | " |
| DCP-A No. 20 | 18 | — | 3050 | 2.882 | 2.5 | 20.1 | 6.9 | " |
| DCP-D No. 2/DCP-A No. 19 | | 8/2 | — | — | — | 5.1 | 5.0 | " |
| DCP-D No. 2/DCP-A No. 19 | | 5/5 | — | — | — | 10.0 | 6.3 | " |

*DCP-D is calcium hydrogenphosphate dihydrate and DCP-A is calcium hydrogenphosphate anhydride.
**measured by the BET method.
***obtained by sieving conventional DCP-A and collecting a fraction having an average particle size of 2 microns.

EXPERIMENTAL EXAMPLE 3

A variety of calcium hydrogenphosphate samples shown in Table 5 were measured for abrasiveness and cleanability by the same methods as used in Experimental Example 1 in order to establish the correlation between physical properties and performance. The results are shown in Table 5.

The calcium hydrogenphosphate samples in Table 5 have physical properties and structure shown in Table 6–8.

TABLE 5

Abrading and cleaning properties of various calcium hydrogenphosphate samples

| Sample | Mixing ratio | Abrasion (RDA value) | Cleanability | |
|---|---|---|---|---|
| DCP-D No. 2 | — | 57 | 2.6 | Comparison |
| DCP-A No. 3 | — | 135 | 4.3 | " |
| DCP-A No. 4 | — | ≧250 | 7.3 | " |
| DCP-D No. 2/ DCP-A No. 4 | 8/2 | 140 | 4.5 | " |
| DCP-D No. 2/ DCP-A No. 4 | 5/5 | 218 | 6.0 | " |
| DCP-A No. 21 | — | 99 | 4.5 | Invention |
| DCP-A No. 22 | — | 121 | 5.8 | " |
| DCP-A No. 23 | — | 145 | 7.0 | " |
| DCP-A No. 24 | — | 174 | 6.6 | " |
| DCP-D No. 2/ DCP-A No. 23 | 5/5 | 130 | 6.6 | " |
| DCP-D No. 2/ DCP-A No. 23 | 9/1 | 73 | 4.3 | " |
| DCP-D No. 2/ DCP-A No. 24 | 5/5 | 140 | 6.1 | " |

TABLE 6

DCP-D: calcium hydrogenphosphate dihydrate

| Sample No. | Average particle size (μm) | Specific surface area (m²/g) |
|---|---|---|
| 1 | 14 | 1.1 |

TABLE 7

DCP-A: calcium hydrogenphosphate anhydride (prior art)

| Sample No. | Average particle size (μm) | Specific surface area (m²/g) | Density (g/cm³) | Average crystallite size (Å) |
|---|---|---|---|---|
| 3 | 2* | 4.4 | 2.89 | 4150 |
| 4 | 16 | 1.2 | 2.89 | 4150 |

*obtained by sieving a prior art DCP-A and collecting a fraction having an average particle size of 2 microns.

TABLE 8

DCP-A: calcium hydrogenphosphate anhydride (invention)

| Sample No. | Average particle size (μm) | Specific surface area (m²/g) | Density (g/cm³) | Average crystallite size (Å) |
|---|---|---|---|---|
| 21 | 3.5 | 3.5 | 2.80 | 1630 |
| 22 | 8 | 3.0 | 2.85 | 2510 |
| 23 | 13 | 3.8 | 2.87 | 3040 |
| 24 | 22 | 11.3 | 2.75 | 910 |

EXPERIMENTAL EXAMPLE 4

The abrasiveness and cleanability of various calcium hydrogenphosphate samples were determined by the same methods as in Experimental Example 2 to establish the correlation between physical properties and performance. The results are shown in Table 9.

The calcium hydrogenphosphate samples in Table 9 have average particle size, average crystallite size, density, specific surface area, and average roundness shown in Tables 10–12.

TABLE 9

Abrasivity on copper plate and cleanability of various calcium hydrogenphosphate samples

| Sample | Mixing ratio by weight | Abrasivity (mg) | Cleanability | |
|---|---|---|---|---|
| DCP-D No. 1 | — | 0.8 | 2.3 | Comparison |
| DCP-D No. 2 | — | 1.2 | 2.5 | " |
| DCP-A No. 3 | — | 17.3 | 4.3 | " |
| DCP-A No. 4 | — | 47.0 | 7.3 | " |
| DCP-D No. 2/ DCP-A No. 4 | 8/2 | 18.5 | 4.5 | " |
| DCP-D No. 2/ DCP-A No. 4 | 5/5 | 31.4 | 6.0 | " |
| DCP-A No. 26 | — | 1.2 | 4.4 | Invention |
| DCP-A No. 27 | — | 2.1 | 5.2 | " |
| DCP-A No. 28 | — | 16.4 | 6.3 | " |
| DCP-A No. 29 | — | 19.0 | 5.8 | " |
| DCP-D No. 2/ DCP-A No. 26 | 5/5 | 1.2 | 4.0 | " |
| DCP-D No. 2/ DCP-A No. 28 | 8/2 | 7.1 | 4.9 | " |
| DCP-D No. 2/ DCP-A No. 28 | 5/5 | 14.9 | 6.0 | " |

TABLE 10

DCP-D: calcium hydrogenphosphate dihydrate

| Sample No. | Average particle size (μm) | Specific surface area (m²/g) | Average roundness |
|---|---|---|---|
| 1 | 9 | 1.2 | 0.38 |
| 2 | 14 | 1.1 | 0.36 |

TABLE 11

DCP-A: platy, angular calcium hydrogenphosphate anhydride

| Sample No. | Average particle size (μm) | Average crystallite size (Å) | Density (g/cm³) | Specific surface area (m²/g) | Average roundness |
|---|---|---|---|---|---|
| 3 | 2* | 4150 | 2.890 | 4.4 | 0.41 |
| 4 | 16 | 4150 | 2.890 | 1.2 | 0.40 |

*obtained by sieving prior art DCP-A and collecting a fraction having an average agglomerate diameter of 2 microns.

TABLE 12

DCP-A: spherulitic calcium hydrogenphosphate anhydride

| Sample No. | Average particle size (μm) | Average crystallite size (Å) | Density (g/cm³) | Specific surface area (m²/g) | Average roundness |
|---|---|---|---|---|---|
| 26 | 17 | 710 | 2.70 | 15.0 | 0.85 |
| 27 | 22 | 1860 | 2.85 | 9.1 | 0.70 |
| 28 | 14 | 2030 | 2.87 | 5.0 | 0.60 |
| 29 | 8 | 2250 | 2.88 | 3.6 | 0.51 |

As seen from the above results, calcium hydrogenphosphate anhydride samples having an average crystallite size of 300 to 3,500 angstroms exhibits a high degree of cleaning action irrespective of low abrasiveness. In the case of calcium hydrogenphosphate dihydrate samples and calcium hydrogenphosphate anhydride samples having an average crystallite size outside the above-defined range, cleanability is proportional to abrasiveness, and thus, abrasiveness must be increased to enhance cleanability.

In the following, this invention will be explained according to examples and comparative examples although this invention is not restricted by these examples.

EXAMPLES 1 TO 6 AND COMPARATIVE EXAMPLES 1 TO 6

Toothpaste compositions containing additives indicated in Table 13 were prepared according to the following prescription and their lustering effects (luster-improving degrees) were investigated. The results are shown in Table 13.

The luster-improving degree was determined by the following method.

| Prescription for Toothpaste | |
|---|---|
| Additive shown in Table 13 | 1.0% |
| Calcium hydrogenphosphate dihydrate | 25.0 |
| Calcium hydrogenphosphate anhydride* | 25.0 |
| Colloidal silica | 2.0 |
| Propylene glycol | 2.0 |
| Sorbitol | 20.0 |
| Sodium carboxy methylcellulose | 1.0 |
| Sodium lauryl sulfate | 1.5 |
| Sodium saccharinate | 0.1 |
| Flavor | 1.0 |
| Preservative | minute quantity |
| Water | Balance |
| | 100.0% |

*Properties of Calcium Hydrogenphosphate Anhydride:
Average particle size 11.0 μm
Average crystallite size 620 Å
Density 2.69 g/cm³
Specific surface area 15.3 m²/g
Average roundness 0.87

LUSTER-IMPROVING DEGREE

A bovine tooth piece cut to a size of 5 mm×5 mm was embedded in a resin, and the bovine tooth enamel was ground to a smooth surface by means of a rotary grinder, and thereafter polished with a No. 1200 emery paper, polished with calcium hydrogenphosphate anhydride, and then buff polished to a gloss of 80.0±2.0 as measured by a gloss meter (GLOSS METER VG-10, manufactured by Nihon Denshoku Kogyo K.K.).

The thus polished bovine tooth piece was then mounted in a polishing tank of a horizontal abrasion tester, into which was poured a suspension of 10 grams of the toothpaste in 30 ml of 40% sorbit solution. The bovine tooth piece was brushed 7000 strokes for 40 minutes in the tester under a load of 200 grams. The brush used was the same as used in Experimental Example 1. At the end of the brushing of 7000 strokes/40 minutes, the gloss of the tooth surface was measured by the gloss meter. The difference between the initial and final gloss values is determined as a gloss increase.

TABLE 13

| No. | Additive | alpha phase content (%) | Average particle size* (μm) | Large particles | Luster-improving degree | Evaluation | |
|---|---|---|---|---|---|---|---|
| 1 | Aluminum oxide | 93 | 1.2 | Eliminating those of more than 5 μm | 20.5 | o | Example 1 |
| 2 | Aluminum oxide | 93 | 2.3 | | 26.2 | o | Example 2 |
| 3 | Aluminum oxide | 78 | 1.8 | Eliminating those of more than 10 μm | 20.8 | o | Example 3 |
| 4 | Aluminum oxide | 52 | 1.8 | | 25.0 | o | Example 4 |
| 5 | Aluminum oxide | 30 | 1.6 | | 23.4 | o | Example 5 |
| 6 | Aluminum oxide | 11 | 2.2 | | 20.0 | o | Example 6 |
| 7 | Aluminum oxide | 93 | 15.1 | | −8.5 | x | Comparative example 1 |
| 8 | Aluminum oxide | 11 | 20.8 | | −15.2 | x | Comparative example 2 |
| 9 | Aluminum oxide | 0 | 0.1 | | 10.5 | x | Comparative example 3 |
| 10 | Titanium oxide | — | 0.2 | | 10.7 | x | Comparative example 4 |
| 11 | Titanium oxide | — | 0.7 | | 11.9 | x | Comparative example 5 |
| 12 | No additions | — | — | | 11.1 | x | Comparative example 6 |

*Measurement of average particle size: a light-transmitting size-distribution-measuring device (Seishin Kigyo-sha Model SKN-1000) was used.

Aluminum oxides with large average particle sizes (No. 7, 8) lowered the luster. Titanium oxide and aluminum oxide with a small average particle size (No. 9) resulted in the same luster as without any addition. In contrast to these results, aluminum oxides used in the examples achieved high luster.

EXAMPLE 7

| | |
|---|---|
| Calcium hydrogenphosphate anhydride* | 20.0% |
| Aluminum oxide** | 1.0 |
| Calcium hydrogenphosphate dihydrate | 20.0 |
| Colloidal silica | 2.0 |
| Propylene glycol | 2.0 |
| Sorbitol | 10.0 |
| Glycerol | 10.0 |
| Sodium carboxy methylcellulose | 0.8 |
| Carrageenan | 0.3 |
| Sodium lauryl sulfate | 1.5 |
| Sodium saccharinate | 0.1 |
| Flavor | 1.0 |
| Preservative | Minute quantity |
| Water | Remaining part |
| | 100.0% |
| Luster-improving degree | 21.3 |

*Properties of Calcium Hydrogenphosphate Anhydride:
| | |
|---|---|
| Average particle size | 17.0 μm |
| Average crystallite size | 1850 Å |
| Density | 2.87 g/cm³ |
| Specific surface area | 3.1 m²/g |
| Average roundness | 0.70 |

**Properties of Aluminum Oxide
| | |
|---|---|
| Average particle size | 1.3 μm |
| (Not containing particles of more than 5 μm.) | |
| Alpha phase content | 93% |

EXAMPLE 8

| | |
|---|---|
| Calcium hydrogenphosphate anhydride* | 10.0% |
| Aluminum oxide** | 2.0 |
| Calcium hydrogenphosphate dihydrate | 30.0 |
| Propylene glycol | 2.0 |
| Glycerol | 25.0 |
| Sodium carboxy methylcellulose | 1.1 |
| Sodium lauryl sulfate | 1.5 |
| Sodium saccharinate | 0.1 |
| Flavor | 1.0 |
| Preservative | Minute quantity |
| Water | Remaining part |
| | 100.0% |
| Luster-improving degree | 22.8 |

*Properties of Calcium Hydrogenphosphate Anhydride:
| | |
|---|---|
| Average particle size | 10.9 μm |
| Average crystallite size | 1650 Å |
| Density | 2.85 g/cm³ |
| Specific surface area | 5.0 m²/g |
| Average roundness | 0.75 |

**Properties of Aluminum Oxide
| | |
|---|---|
| Average particle size | 1.6 μm |
| (Not containing particles of more than 10 μm.) | |
| Alpha phase content | 30% |

EXAMPLE 9

| | |
|---|---|
| Calcium hydrogenphosphate anhydride* | 42.0% |
| Aluminum oxide** | 3.0 |
| Glycerol | 25.0 |

| -continued | |
| --- | --- |
| Sodium carboxy methylcellulose | 1.1 |
| Sodium lauryl sulfate | 1.0 |
| Sucrose monolaurate | 0.5 |
| Sodium saccharinate | 1.0 |
| Flavor | 1.0 |
| Preservative | Minute quantity |
| Water | Remaining part |
| | 100.0% |
| Luster-improving degree | 20.1 |

*Properties of Calcium Hydrogenphosphate Anhydride:

| | |
| --- | --- |
| Average particle size | 20.1 μm |
| Average crystallite size | 2510 Å |
| Density | 2.88 g/cm$^3$ |
| Specific surface area | 2.8 m$^2$/g |
| Average roundness | 0.65 |

**Properties of Aluminum Oxide

| | |
| --- | --- |
| Average particle size | 1.8 μm |
| (Not containing particles of more than 10 μm.) | |
| Alpha phase content | 78% |

What is claimed is:

1. A dentifrice composition comprising: calcium hydrogenphosphate anhydride whose crystallite has an average size of 300 to 3,500 angstroms as measured by X-ray diffractometry wherein the calcium hydrogenphosphate anhydride has a density of 2.650 to 2.885 g/cm$^3$, a specific surface area of 2.5 to 20 m$^2$/g as measured by the BET method, and an average particle size of 2 to 30 μm; and an aluminum oxide having an average particle size of 0.5 to 10 μm.

2. A dentifrice composition according to claim 1 wherein the aluminum oxide has an average particle size of 0.5 to 5 μm.

3. A dentifrice composition according to claim 1 wherein the aluminum oxide does not contain large particles of more than 10 μm.

4. A dentifrice composition according to claim 1 wherein the aluminum oxide has an alpha phase content of below 93%.

5. A dentifrice composition according to claim 1 wherein the blending amount of the calcium hydrogenphosphate anhydride is in the range of 1 to 60% by weight of the composition and the blending amount of the aluminum oxide is in the range of 0.1 to 30% by weight of the composition.

6. A dentifrice composition according to claim 1 wherein the ratio by weight of the calcium hydrogenphosphate anhydride to the aluminum oxide is in the range of 100:0.2 to 100:60.

7. A dentifrice composition according to claim 1, wherein the aluminum oxide has an alpha phase content of between 90% and 10%.

8. A dentifrice composition according to claim 1, wherein the aluminum oxide has an alpha phase content of between 85% and 15%.

9. A dentifrice composition according to claim 1, wherein the aluminum oxide is present in an amount of 0.3 to 10% by weight.

10. A dentifrice composition according to claim 1, wherein said calcium hydrogenphosphate anhydride is present in an amount of 5 to 50% by weight.

11. A dentifrice composition, comprising: 1 to 60% by weight of the composition of calcium hydrogenphosphate anhydride whose crystallite has an average size of 300 to 3,500 angstroms as measured by X-ray diffractometry and having a density of 2.650 to 2,885 g/cm$^3$, a specific surface area of 2.5 to 20 m$^2$g as measured by the BET method and an average particle size of 2 to 30 μm; and 0.1 to 30% by weight of the composition of an aluminum oxide having an average particle size of 0.5 to 10 μm and an alpha phase content of below 93%, wherein the ratio by weight of the calcium hydrogenphosphate anhydride to the aluminum oxide is in the range of 100:0.6 to 100:20.

* * * * *